United States Patent
Sultan et al.

(10) Patent No.: US 8,696,590 B1
(45) Date of Patent: Apr. 15, 2014

(54) INSTRUMENTATION FOR SMALL-ANIMAL CAPNOMETRY

(75) Inventors: Firas Sultan, Brookfield, WI (US); David P. Klemer, Whitefish Bay, WI (US)

(73) Assignee: Criticare Systems, Inc., Waukesha, WI (US)

( * ) Notice: Subject to any disclaimer, the term of this patent is extended or adjusted under 35 U.S.C. 154(b) by 501 days.

(21) Appl. No.: 12/819,961

(22) Filed: Jun. 21, 2010

Related U.S. Application Data

(60) Provisional application No. 61/269,081, filed on Jun. 19, 2009.

(51) Int. Cl.
*A61B 5/093* (2006.01)
*A61B 5/095* (2006.01)

(52) U.S. Cl.
USPC ........... 600/532; 600/301; 600/529; 600/540; 600/541; 600/542; 600/543; 128/203.12

(58) Field of Classification Search
USPC .......................... 600/301, 529, 532, 540–543; 128/203.12
See application file for complete search history.

(56) References Cited

U.S. PATENT DOCUMENTS

| | | | | |
|---|---|---|---|---|
| 4,332,244 A | * | 6/1982 | Levy et al. | 128/205.25 |
| 6,349,725 B1 | * | 2/2002 | Perkins et al. | 128/206.21 |
| 2004/0216737 A1 | * | 11/2004 | Anderson et al. | 128/203.12 |
| 2006/0278218 A1 | * | 12/2006 | Hoffman | 128/200.24 |
| 2008/0168948 A1 | * | 7/2008 | Truitt et al. | 119/417 |
| 2009/0084378 A1 | * | 4/2009 | Ichikawa | 128/203.12 |
| 2009/0151720 A1 | * | 6/2009 | Inoue et al. | 128/203.12 |

* cited by examiner

*Primary Examiner* — Jacqueline Cheng
*Assistant Examiner* — Puya Agahi
(74) *Attorney, Agent, or Firm* — Factor Intellectual Property Law Group, Ltd.

(57) ABSTRACT

Vital sign monitoring is especially challenging in small animals, given the high metabolic rates and small volumes under consideration. An embodiment of the present invention includes a unique nose-cone design and associated instrumentation which allows for measurement of respiratory parameters, including anesthesia gas concentration, inspiratory and expiratory $O_2$, and inspiratory and expiratory $CO_2$ (capnometry). Such instrumentation facilitates a physiologic assessment of small animals undergoing general anesthesia, an increasingly important consideration as small animals play a greater role in in vivo biomedical studies. In addition, the techniques proposed herein are suitable for measurement on small respiratory volumes associated with neonatal monitoring.

10 Claims, 5 Drawing Sheets

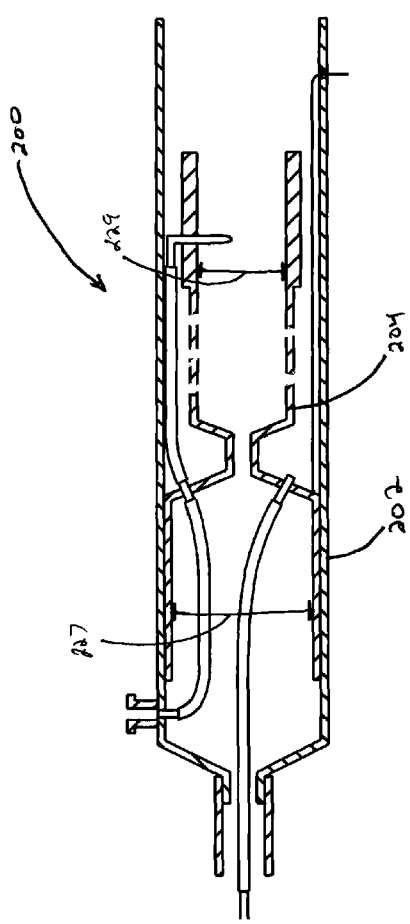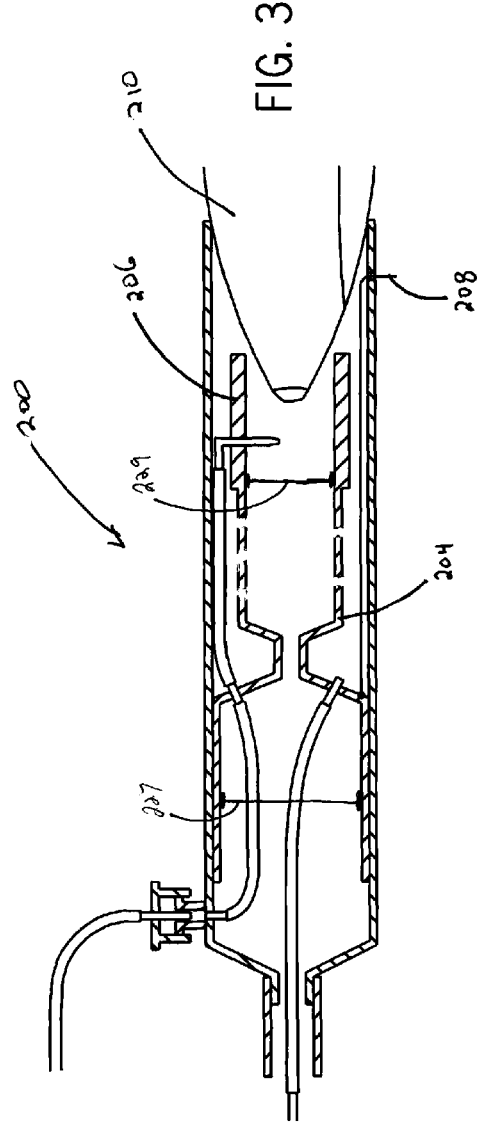

INSTRUMENTATION FOR SMALL-ANIMAL CAPNOMETRY

CROSS-REFERENCE TO RELATED APPLICATIONS

This patent application claims priority of U.S. Provisional Patent Application No. 61/269,081 entitled "Instrumentation for Small-Animal Capnometry," and which was filed on Jun. 19, 2009, the entirety of which patent application is hereby incorporated herein by reference.

BACKGROUND OF THE INVENTION

Field of the Invention

The present invention relates generally to monitoring, and more particularly to monitoring of small animal physiologic respiration.

Monitoring of human vital signs, including heart rate, respiratory rate, hemoglobin oxygen saturation and others, has become an indispensable part of the standard of care in a hospital setting. For example, vital sign monitoring during administration of general anesthesia is essential, given the role that the anesthesiologist plays in assuming physiologic control. The importance of physiologic monitoring in a hospital setting is obvious; no hospital patient undergoing surgery would argue with the need for the anesthesiologist to closely monitor numerous vital sign parameters during administration of general anesthesia. Likewise, the need for vital sign monitoring of patients in an intensive-care unit is also clear, given the fact that the hospital intensivist may be assuming full control of respiratory rates, volumes, pressures and inhaled gas concentrations for ventilator-dependent patients.

In veterinary settings, however, electronic physiologic monitoring typically plays less prominent a role. For simple procedures under general anesthesia, a veterinarian may simply use a visual observation of respiratory rate as an indicator of depth of anesthesia. While the historic reasons for the relative absence of veterinary physiologic monitoring instrumentation may partially relate to cost, the technical difficulties associated with measurement of small quantities and volumes are also an important factor. For example, the tidal volumes associated with respiration in a rat may be as low as 600 microliters almost three orders of magnitude smaller than the typical 500 milliliter respiratory tidal volume for a young man. (See, Sharp P E and M C LaRegina, *The Laboratory Rat*, CRC Press, Boca Raton, 1998, pp 10-11; and Guyton AC and J E Hall, *Textbook of Medical Physiology*, 9ed, WB Saunders Co, Philadelphia, 1996, pp 482-486.) In addition, the elevated metabolic rates in small animals—heart rates as high as 450 beats per minute and respiratory rates as high as 115 breaths per minute also place demands on the sampling instrumentation which is required to convert time-varying physiologic variables into useful electronic signals. (See, Sharp P E and M C LaRegina, *The Laboratory Rat*, CRC Press, Boca Raton, 1998, pp 10-11.) For this reason, scaling of physiologic monitoring instrumentation designed for humans to the small-animal veterinary domain is not a trivial undertaking.

Small animals play an increasingly vital role in assisting biomedical researchers with validation of new medical advances and technologies, such as novel experimental imaging modalities. As an example, full physiologic monitoring is not uncommon for rodents undergoing functional magnetic resonance imaging (fMRI) in high-field MR scanners. Such animals are typically sedated or anesthetized during an imaging session, and physiologic monitoring may be used for confirmation of animal safety and well-being, as well as for synchronization and gating of imaging acquisition signals.

Several manufacturers (e.g., Kent Scientific, Harvard Apparatus) do make highly specialized instrumentation specifically for small-animal respiratory measurements, however, this equipment may be specialized and expensive.

Thus, it would be advantageous to provide a capnometry apparatus that would allow for physiologic measurement on small respiratory volumes. It would further be advantageous to provide a capnometry apparatus that allows for respiratory monitoring of small mammalian subjects. It would also be advantageous to take physiologic measurements on small respiratory volumes using standard human physiologic monitoring equipment.

SUMMARY OF THE INVENTION

Designs of instrumentation intended for real-time measurement of physiologic respiratory parameters in rodents and other small animals undergoing general anesthesia, focusing attention on inspiratory and expiratory gas concentrations (anesthetic agent as well as $O_2$ and $CO_2$ concentrations) are described herein. In addition, an embodiment of the present invention regarding physiologic measurement on small respiratory volumes may also be directly adapted to neonatal monitoring. An embodiment of the capnometry apparatus described herein allows instrumentation designed for humans to be easily adapted to small animal measurements, with the simple addition of a novel, low-cost nose cone.

The disadvantages and limitations of the background art discussed above can be overcome by the present invention. With this invention, a small animal capnometry apparatus can be configured for use with physiologic monitoring equipment. Such an apparatus can comprise a first chamber comprising a first volume and a first cross-sectional dimension, a second chamber in fluid communication with the first chamber and including a second volume and a second cross-sectional dimension. The second chamber can be sized to receive a nare of a small animal. such an apparatus can comprise a respiratory gas sampling conduit having a first end and a second end, with the first end coupled to the second chamber proximate a small animal nare positioned therein and the second end configured to couple to a human physiologic monitoring system to provide a respiratory sample from a small animal nare.

In another aspect, a capnometry system for monitoring pulmonary tidal volumes between approximately 0.6 and 2.0 millimeters using monitoring equipment is provided. Such a system can comprise a first chamber having a first volume and first cross-sectional dimension, a second chamber in fluid communication with the first chamber and proximate a subject configured to receive a sample and having a second volume and a second cross-sectional dimension. Such a system can also comprise a sampling conduit having a first end and a second end, the first end being coupled to the standard human physiologic monitoring equipment and the second end being configured within the first chamber proximate a sample source. Such a first volume can be larger than such a second volume and such a first cross-sectional dimension can be larger than such a second cross-sectional dimension.

In another aspect, a method of affecting the sensitivity of standard human physiologic monitoring equipment is provided. Such a method can comprise the steps of providing a capnometry apparatus including a first chamber having a first cross-sectional dimension, a second chamber having a second cross-sectional dimension and being in fluid communication with the first chamber by a connecting portion having a third cross-sectional dimension, and a sampling conduit having a first end in fluid communication with the second chamber and a second end coupled to the human physiologic monitoring equipment. Such a method can comprise positioning the second chamber proximate to a nare of a mammalian subject, introducing anesthesia gas to the second chamber, sampling respiratory gas from the second chamber using the sampling conduit to provide the sample to the standard human physiologic monitoring equipment, and withdrawing respiratory gas and residual anesthesia gas from the first chamber. Such an introduction of anesthesia gas and withdrawal of expiratory and residual anesthesia gas can be independently controlled.

Such a capnometry apparatus of the present invention can be of a construction which is both durable and long lasting, and which can require little or no maintenance to be provided by the user throughout its operating lifetime. Such a capnometry apparatus of the present invention can also be of inexpensive construction to enhance its market appeal and to thereby afford it the broadest possible market. Finally, all of the aforesaid advantages and objectives are achieved without incurring any substantial relative disadvantage.

DESCRIPTION OF THE DRAWINGS

These and other advantages of the present invention are best understood with reference to the drawings, in which:

FIG. 2 is a longitudinal cross-sectional view of an embodiment of a nose cone of the present invention at the midplane of the nose cone.

FIG. 3 is a longitudinal cross-sectional view of an embodiment of the nose cone of FIG. 2 in use, including a schematic illustration of the components of the nose cone.

DETAILED DESCRIPTION OF THE EXEMPLARY EMBODIMENTS

In one embodiment the present invention addresses the low volumes associated with small animal respiration, for which pulmonary tidal volumes fall in the range 0.6-2.0 milliliters. A similar approach may also be used in neonatal applications, where respiratory volumes are also low. (See Jagerty J J, M E Klineman, D Zurakowski, A C Lyons and Krauss B, "Accuracy of a new low-flow sidestream capnography technology in newborns: a pilot study," J Perinatol, 22(3), April-May 2002, pp 219-25.) Tidal volume is defined as the magnitude of the difference between lung volume at the end of inspiration and lung volume at end of expiration, for "normal" unforced breathing:

$$V_T = V_{i,end} - V_{e,end} \quad (1)$$

where $V_T$ is the tidal volume, $V_{i,end}$ is the end-inspiratory volume, and $V_{e,end}$ is the end-expiratory volume. (See Guyton A C and J E Hall, *Textbook of Medical Physiology*, 9ed, WB Saunders Co, Philadelphia, 1996, pp 482-486.) Simple scaling of respiratory instrumentation and face masks used in humans will not suffice for small animals, since the gas flows involved are much larger in humans when compared to respiratory gas flows encountered in small animals.

Figure 1:
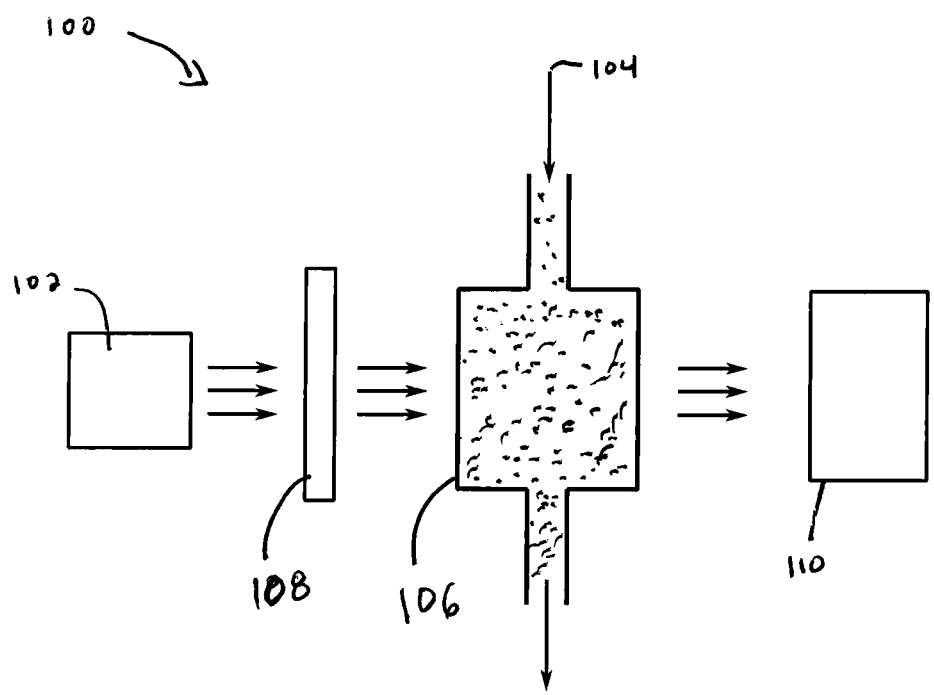
FIG. 1 is a general schematic illustration of an infrared absorbance cell.

Before addressing an embodiment of the present invention for increasing the sensitivity of instrumentation to the small volumes encountered in rodents, it may be instructive to review the typical approach for measurement of respiratory gas concentrations. (See Marin, P L, *The ICU Book*, Williams and Wilkins, Baltimore, 1998, p 355.) FIG. 1 illustrates the typical spectroscopic approach: an optical source 102 is used to illuminate a gas 104 being measured in a precisely-defined flow cell 106 which is essentially transparent to specific wavelength(s) used for the measurement. A narrow bandpass filter (or filters) 108 is used to select a specific wavelength, and the optical absorption of the gas is determined using an electronic photodetector 110. Optical absorption follows the Beer-Lambert Law, see Prasad, P N, *Introduction to Biophotonics*, John Wiley and Sons, Hoboken, 2003, pp 105-106:

$$I_{det}(\lambda) = I_o(\lambda)^{-k(\lambda)bc}, \quad (2)$$

where $k(\lambda)$ is the extinction coefficient of the gas at a wavelength $\lambda$, b is the optical path length of the flow cell, and c is the concentration of the absorbing gas.

Thus, a measurement of $I_{det}/I_o$ allows one to calculate the unknown concentration c, assuming a priori knowledge of b and k. In practice, sample respiratory gas is withdrawn from a closely-fitting face mask, preferably as close to the nares as possible, and wavelengths used for the measurement typically fall in the infrared region of the spectrum. (See Marin, P L, *The ICU Book*, Williams and Wilkins, Baltimore, 1998, p 355.) In small animals, respiratory gas volumes are quite small and easily overwhelmed by the delivery of anesthetic agent and oxygen carrier gas.

To address this problem, an embodiment of the present invention includes a novel nose cone design which permits concentration of expired gas in a small inner chamber, from which the sampled gas is withdrawn for measurement.

FIG. 2 illustrates one embodiment of a cylindrical nose cone 200, which includes a larger outer shell 202 enclosing a smaller (but relatively tight-fitting) inner cylinder 204 which can be adjusted in longitudinal position within the outer cylinder 202. FIG. 2 represents a longitudinal cross-section at the midplane of the nose cone 200.

FIG. 3 illustrates an embodiment of the nose cone 200 in use, as well as a schematic illustration of various components of an embodiment of the nose cone 200. Contact with the rodent face and nose is made with an open silicone cylinder 206 terminating the administration end of the inner sliding cylinder 204. A drawstring 208 is used to pull the inner cylinder 204 into proximity with the rodent 210; the soft silicone ensures that there is no traumatic injury to the rodent nose.

Figure 4:
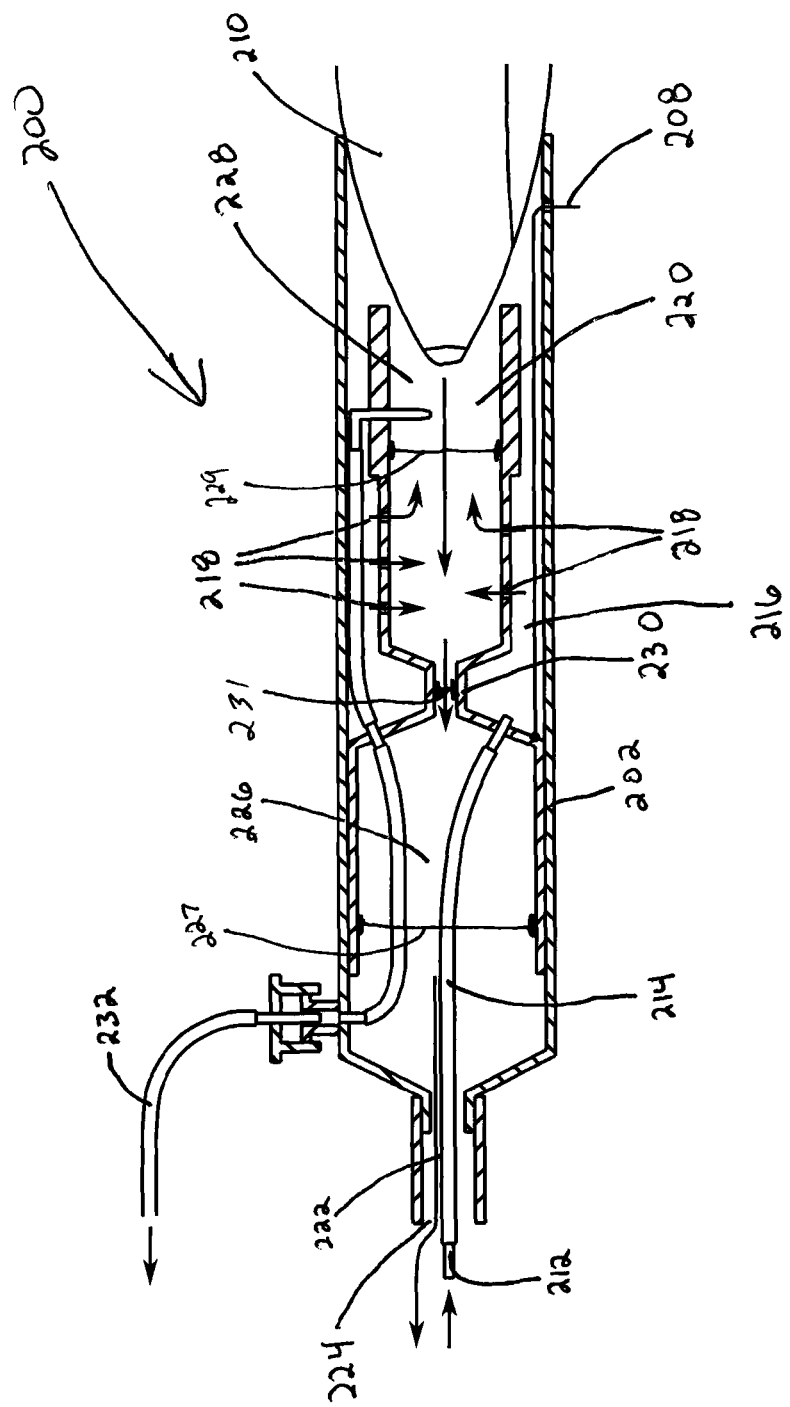
FIG. 4 is a longitudinal cross-sectional view of an embodiment of the nose cone of FIG. 2 in use, including a schematic illustration of the components of the nose cone and inlet, exhaust, and sampled gas flows during anesthesia administration.

Without limitation to any one theory or mode of operation, FIG. 4 illustrates the gas flow dynamics during use of an embodiment of the nose cone 200. An anesthesia gas/oxygen mixture is delivered to the anesthesia inlet port 212, and the gas is directed through small tubing 214 to an area 216 just external to the inner sliding cylinder 204. Open ports 218 allow the anesthesia gas to diffuse into the inner cylinder lumen 220 for rodent inspiration. Expiratory gases and superfluous anesthesia gas are exhausted through a central bore 222, and drawn into a low (fumehood) vacuum through tubing connected at a port 224 proximate the inlet port 212.

In one embodiment, the inner cylinder 204 is divided into a larger chamber, sometimes herein referred to as a larger vacuum chamber 226 distal from the animal nose, and a smaller proximal sampling chamber 228, proximate the animal nose. The two chambers 226, 228 are connected by a vacuum constriction 230, in one embodiment, approximately 2-3 mm in diameter. The larger vacuum chamber 226 defines a first volume and a first cross-sectional dimension 227. The smaller proximal sampling chamber 228 defines a second volume and a second cross-sectional dimension 229. In one embodiment, the first volume and the first cross-sectional dimension 227 are larger than the second volume and the second cross-sectional dimension 229. The vacuum constriction 230 defines a third cross-sectional dimension 231 preferably smaller than the first cross-sectional dimension 227 and the second cross-sectional dimension 229.

In one embodiment, the larger vacuum chamber 226 is configured for application of a pressure thereon, the pressure in one embodiment being less than or equal to the atmospheric or ambient pressure. The pressure applied may be negative. The pressure applied may also be equal to the atmospheric or ambient pressure.

The arrangement of the larger vacuum chamber 226 and the smaller proximal sampling chamber 228 allows for independent control of the pressure/flow rate of the applied anesthesia gases which reach the proximal sampling chamber 228, and the magnitude of the exhausting vacuum which is applied to the inner distal vacuum chamber 226 (discussed further below).

Another small section of tubing 232 is connected to the capnometer, in one embodiment, such as the one illustrated in FIG. 1 and, under capnometer-supplied vacuum, a sample of gas very close to the rodent nares is withdrawn and passed to, for example, the absorbance cell 106 in a standard (human) physiologic monitoring system 100 (see FIG. 1). The gas withdrawal rate is adjustable from 100 to 200 ml/minute.

Figure 5:
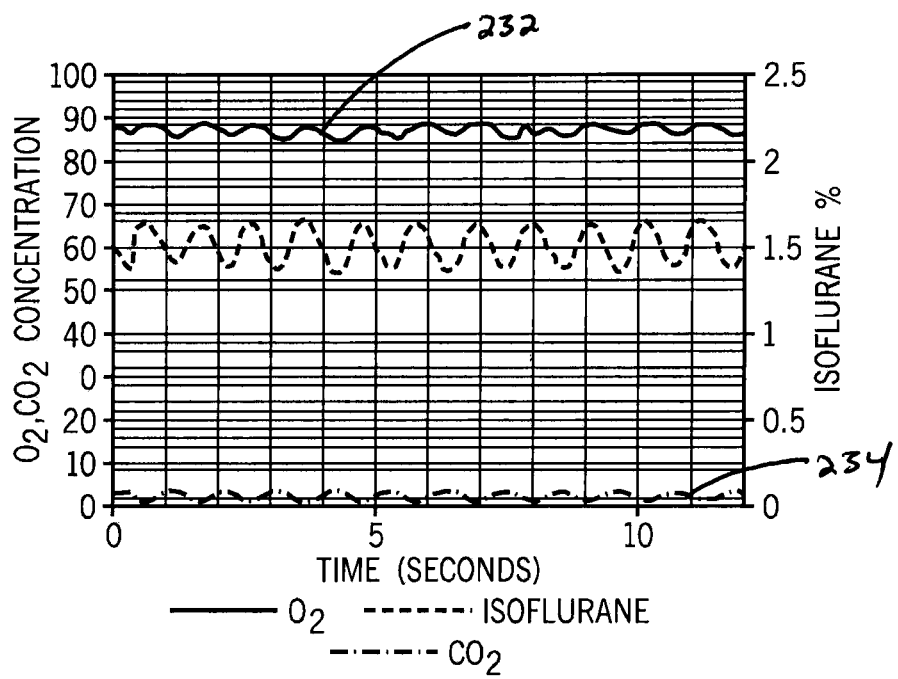
FIG. 5 is a graph of exemplary rodent respiratory waveforms under 1.5% isoflurane anesthesia.

FIG. 5 illustrates an exemplary rodent respiratory waveform under 1.5% isoflurane anesthesia when a 100 ml/min withdrawal rate was used. Given the small volume within the inner sampling chamber 220, this sample gas is quite representative of the rodent respiratory gases on inspiration and expiration. The mixing of inspiratory and expiratory gases may occur in the sampling chamber 220, but careful independent adjustment of applied anesthesia gas flow rate and exhaust vacuum can minimize this effect, as could be easily determined without undue experimentation by one having ordinary skill in the art.

Measurements

Validation of the measurement instrumentation and an embodiment of the nose cone 200 was accomplished under rodent anesthesia using isoflurane anesthesia, under an approved animal protocol. A female Sprague-Dawley rat approximately eight weeks of age was used in the validation. Research personnel included an engineer responsible for instrument testing, and a researcher with sole responsibility for anesthesia administration, monitoring of anesthesia depth and animal safety. Capnometry and anesthesia gas concentrations were recorded by a flow (absorbance) cell interrogated by a specially-modified Poet IQ2 Anesthesia Gas Monitor provided by Criticare Systems, Inc.

FIG. 5 illustrates results of a measurement for which isoflurane concentration was 1.5%, with oxygen administered at a rate of 2 liters/min. As expected, the oxygen 232 and $CO_2$ 234 waveforms are out of phase by 180 degrees, with $O_2$ reaching its peak at end-inspiration, and $CO_2$ reaching a peak at end-expiration. (By definition, end-expiration occurs when $CO_2$ reaches a maximum.) Likewise, peak values for isoflurane coincide with $O_2$ peaks at end-inspiration, and isoflurane minima occur at end-expiration. The difference between isoflurane peak and trough represents biologic uptake of isoflurane. In this measurement, respiratory rate was 52 breaths/minute. The monitor indication agreed with the visually-observed respiratory rate.

Figure 6:
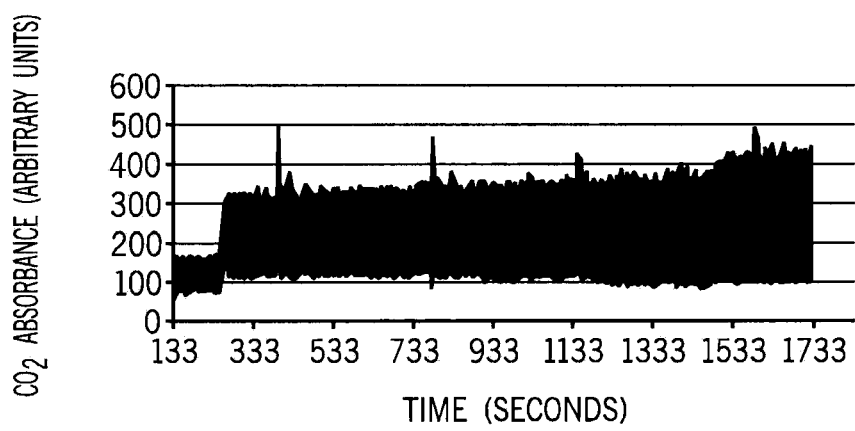
FIG. 6 is a long time axis graph of a $CO_2$ waveform.
Figure 7:
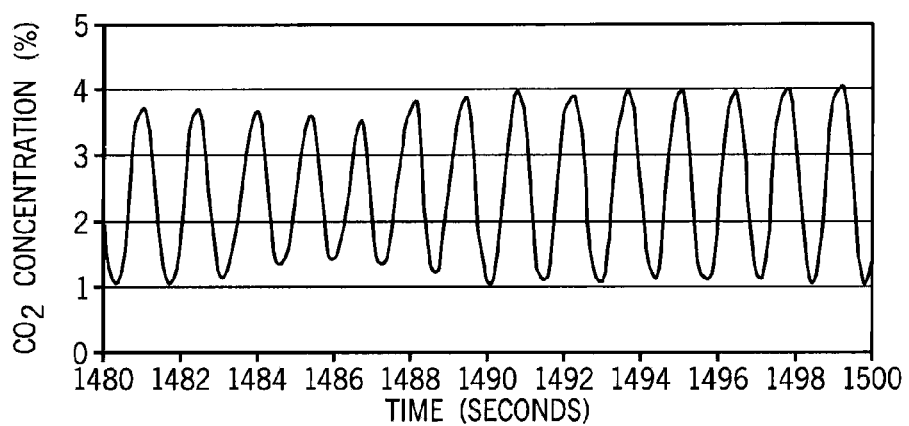
FIG. 7 is a fast time scale graph of a $CO_2$ waveform.

Expiratory $CO_2$ waveforms are shown over two time scales in FIGS. 6 and 7, with one unit on the horizontal axis representing one second. FIG. 6a represents the entire 30-minute anesthesia session. There are advantages associated with viewing data like this at various time scales. On a fast scale, as illustrated in FIG. 7, breath-to-breath variations can be seen, and anomalous breathing patterns (e.g., Cheyne-Stokes respiration, see Bates B, L S Bickley, R A Hoekelman and J E Thompson, *A Guide to Physical Examination and History Taking*, 6ed, JP Lippincott Co, Philadelphia, 1995, p 252) can easily be recognized. On a long time axis, as illustrated in FIG. 6, the trend in increasing levels of $CO_2$ is obvious, associated with an anesthetic-induced decrease in respiratory rate.

Figure 8:
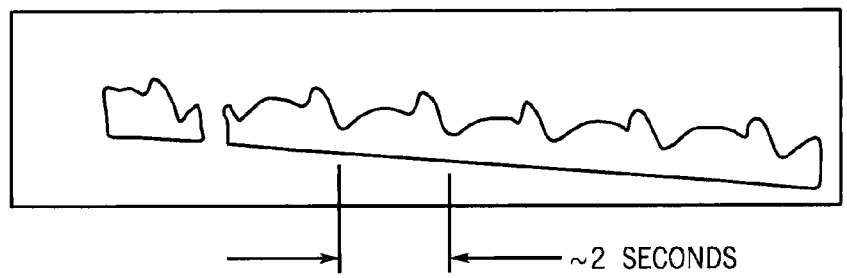
FIG. 8 is a detailed view of the expiratory $CO_2$ waveform at a deep level of anesthesia.

Finally, as anesthesia depth increases, the capnographic waveform shows marked changes, as illustrated in the FIG. 8, recorded directly from the nCompass Vital Signs Monitor screen. At slow respiratory rates, a marked increase in end-expiratory $CO_2$ is evident, perhaps reflecting greater $CO_2$ concentrations associated with pulmonary/alveolar dead space, more noticeable at low respiratory rates.

It is clear that there is a wealth of information carried in respiratory capnometric waveforms: metabolic activity, depth of anesthesia, oxygen/carbon dioxide exchange and respiratory rate.

Such information is not only useful for monitoring of animal health and well-being while under anesthesia, but can also indicate pathology or disease states—e.g., manifestations of impaired oxygen exchange during acute pulmonary edema. Because the rates and volumes are much smaller than those of humans, simple scaling of physiologic monitoring instrumentation to small-animal dimensions may be unsatisfactory. An embodiment of a small animal nose cone 200 of the present invention can allow for appropriate sampling of the small volumes which are associated with rodent respiration, even without significant modification of existing, commercially-available electronic sampling circuitry, such as, for example, that illustrated in FIG. 1. Adaptation of an embodiment of this nose cone 200 to conventional respiratory and anesthesia monitoring instrumentation can successfully permit the acquisition of useful physiologic waveforms.

For purposes of this disclosure, the term "coupled" means the mechanical joining of two components directly or indirectly to one another. Such joining may be stationary in nature or moveable in nature. Such joining may be achieved with the two components and any additional intermediate members being integrally formed as a single unitary body with one another or the two components and any additional member being attached to one another. Such joining may be permanent in nature or alternatively be removable or releasable in nature.

Although the foregoing description of the bait station kit of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

What is claimed is:

1. A small animal capnometry apparatus configured for use with a monitoring equipment, the apparatus comprising:
   a first chamber comprising a first volume and a first cross-sectional dimension;
   a second chamber in fluid communication with the first chamber, the second chamber comprising a second volume and a second cross-sectional dimension, the second chamber being sized to receive a nare of a small animal;
   a respiratory gas sampling conduit having a first end and a second end, the first end coupled to the second chamber proximate a small animal nare positioned therein, the second end for coupling to a monitoring system to provide a respiratory gas sample from a small animal nare;
   an outer fixed cylinder arranged and configured around the first chamber and the second chamber, the outer fixed cylinder defining an anesthesia access port;
   an anesthesia gas exhaust conduit and an anesthesia gas inlet conduit, the anesthesia gas inlet conduit comprising a delivery end positioned between the outer fixed cylinder and the first and second chambers, wherein the second chamber defines at least one open port configured to allow anesthesia gas to diffuse into the second chamber for inspiration by a small animal, the first end of the respiratory gas sampling conduit being positioned closer to a small animal nare than the at least one open port; and
   a connector component disposed between the first chamber and the second chamber, and spaced apart from the at least one open port, the connector component defining a third cross-sectional dimension smaller than each of the first cross-sectional dimension and the second cross-sectional dimension.

2. The apparatus of claim 1, wherein the second volume is less than the first volume and the second cross-sectional dimension is less than the first cross-sectional dimension.

3. The apparatus of claim 1, wherein the second chamber is slidingly displaceable relative to the outer fixed cylinder.

4. The apparatus of claim 3, comprising a flexible locating drawstring coupled to at least one of the first chamber and the second chamber, the flexible locating drawstring configured to slidingly displace the second chamber relative to the outer fixed cylinder, for selectively positioning the second chamber relative to a small animal nare.

5. The apparatus of claim 1, wherein the monitoring equipment comprises standard human physiologic monitoring equipment.

6. The apparatus of claim 1, comprising a silicone cylinder coupled to and terminating the end of the second chamber proximate a small animal nare.

7. The apparatus of claim 1, wherein the monitoring equipment comprises an anesthesia gas monitor.

8. The apparatus of claim 7, comprising a vital signs monitor screen configured to display measurements recorded by the anesthesia gas monitor.

9. The apparatus of claim 1 wherein the first end of the sampling conduit is directly coupled to the second chamber.

10. The apparatus of claim 1 wherein the second chamber defines at least two open ports for allowing anesthesia to diffuse into the second chamber for inspiration by a small animal, the first end of the sampling conduit being positioned closer to a small animal nare than each of the at least two open ports.

* * * * *